United States Patent [19]

Penney

[11] Patent Number: 5,194,882
[45] Date of Patent: Mar. 16, 1993

[54] KERATOGRAPHIC INSTRUMENT USING HOLOGRAPHIC PLACIDO ILLUMINATOR TO REDUCE ALIGNMENT SENSITIVITY

[75] Inventor: Carl M. Penney, Saratoga Springs, N.Y.

[73] Assignee: General Electric Company, Schenectady, N.Y.

[21] Appl. No.: 709,544

[22] Filed: Jun. 3, 1991

[51] Int. Cl.$^5$ .................... A61B 3/107; G03H 1/00
[52] U.S. Cl. ........................... 351/212; 351/221; 351/246; 359/1; 359/19
[58] Field of Search ............... 351/211, 212, 221, 246, 351/220; 359/1, 19

[56] References Cited

U.S. PATENT DOCUMENTS

| | | | |
|---|---|---|---|
| 4,569,576 | 2/1986 | Karpov et al. | 351/212 |
| 4,662,730 | 5/1987 | Outwater et al. | 351/212 |
| 4,863,260 | 9/1989 | Gersten et al. | 351/246 X |
| 4,917,458 | 4/1990 | Matsumura | 351/212 |

Primary Examiner—Bruce Y. Arnold
Assistant Examiner—David R. Parsons
Attorney, Agent, or Firm—James R. McDaniel; Paul R. Webb, II

[57] ABSTRACT

A hologram is used to project an image of a pattern similar to a placido upon the cornea of a subject. By viewing the reflection of the pattern in the subject's cornea, one may measure the curvature of the cornea. The use of the hologram in the keratometer system allows the pattern to be imaged at infinity, thereby minimizing any error which might otherwise result from incorrect assumptions about the cornea position.

20 Claims, 2 Drawing Sheets

KERATOGRAPHIC INSTRUMENT USING HOLOGRAPHIC PLACIDO ILLUMINATOR TO REDUCE ALIGNMENT SENSITIVITY

BACKGROUND OF THE INVENTION

The present invention relates to keratographic instruments used for measurement of the cornea of an eye. More specifically, the present invention relates to such instruments having an illumination arrangement to reduce alignment sensitivity.

A keratometer measures the curvature of the cornea at one or several radial positions with respect to an eye axis defined by eye orientation. The eye axis is usually close to the visual axis. The keratometer provides a keratograph showing the curvature of the cornea at many points, the points being densely distributed over a moderate to large fraction of the cornea.

There are several types of keratographs in use or proposed for use. Most of these have a light source in the form of a set of rings with progressively greater diameters, the rings being concentric about a common axis. The image of the corneal reflection of these rings is observed by a camera and analyzed to determine corneal shape at multiple points.

Some modern versions of the keratometer use a TV camera to view the image of the rings of light in the subject's eye and digitize the image for computer analysis of the cornea shape. Unfortunately, errors are introduced into this information if the cornea is displaced from the position assumed in the calculations. That is, the image of a light which has been reflected by a cornea has a pattern which depends upon the contour of the cornea and the position of the cornea. To the extent that the cornea position may be different from that assumed by the calculations, an instrument will introduce an inaccuracy in the calculations of the cornea shape. Since the inaccuracy in cornea shape due to slight displacement of the cornea from an assumed position can be shown geometrically to increase as the light source gets closer to the eye, one would want the light source to be relatively far away from the cornea of the eye. However, moving the light source far away from the observed eye will restrict the field of view of the cornea of the eye because the light of some rings will be interrupted by the nose and brows of the person.

Among prior patents for cornea curvature measurements, U.S. Pat. No. 4,662,730 issued May 5, 1987 to Outwater shows a scanning keratometer using a holographic element functioning as a lens to scan a beam of light over the cornea, and to descan the light scattered back from the beam by the cornea.

OBJECTS AND SUMMARY OF THE INVENTION

Accordingly, it is a primary object of the present invention to provide a new and improved keratographic instrument and associated system and method.

A more specific object of the present invention is to provide for the measurement of the cornea with little or no error arising from displacement of the cornea from an assumed position and, at the same time, avoiding restrictions on the field of view of the cornea which might arise from the nose and brows of the subject.

A further object of the present invention is to provide for accurate measurements of the cornea, while allowing one to use currently existing TV camera and computer vision processing methods. In other words, the present invention relies upon a change in only a portion of currently used systems and allows one to continue to use most of the other components of currently used keratometer arrangements.

The above and other objects of the present invention may be realized by a system for measuring the curvature of a cornea having a hologram for generating a cornea measurement pattern image which appears to emanate from a relatively distant region from a subject's eye even though the hologram is relatively close to a subject's eye, such that a reflection of the pattern image on the cornea of the subject's eye is established. (As used herein, a "pattern" requires at least two points which are simultaneously visible.) A light source is used to apply light to the hologram so as to cause it to project the pattern image. The hologram has a window disposed therein. (As used herein, "window" shall include an opening or hole as well as transparent material.) The window in the hologram is preferably an opening. The system may further include a reflector such that light from the light source is applied to the hologram by way of reflection from the reflector. The reflector may have a window disposed therein, which window is preferably an opening. The system may further include a viewing subsystem for viewing the reflection of the pattern image in the cornea. The viewing subsystem preferably includes a camera, a monitor, and a vision processor for determining cornea curvature based on the reflection of the pattern image on the cornea. The viewing subsystem views the reflection of the pattern image on the cornea by way of the window in the reflector and the window in the hologram. The hologram is between the pattern image and the eye. The hologram projects the pattern image imaged at infinity. The pattern image preferably includes a plurality of rings. The light source applies a fixed beam of light to the hologram, meaning that the beam is not a scanned beam. The light source is a laser. The system may further include a means to receive and broaden a beam from the laser before applying a broadened beam to the hologram. The means to receive and broaden is preferably a telescope.

The method of the present invention includes the placing of a hologram relatively close to a subject's eye, and applying light to the hologram to generate a cornea measurement pattern image which appears to emanate from a relatively distant region from a subject's eye such that a reflection of the pattern image on the cornea of the subject's eye is established. The hologram is preferably placed between the subject's eye and nose, meaning that at least some lines from the tip of the subject's nose towards the subject's eye will intersect the hologram. The pattern image is preferably imaged at infinity. The light is preferably applied from a laser. The method further includes the step of viewing the reflection of the pattern image on the cornea to determine cornea curvature.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
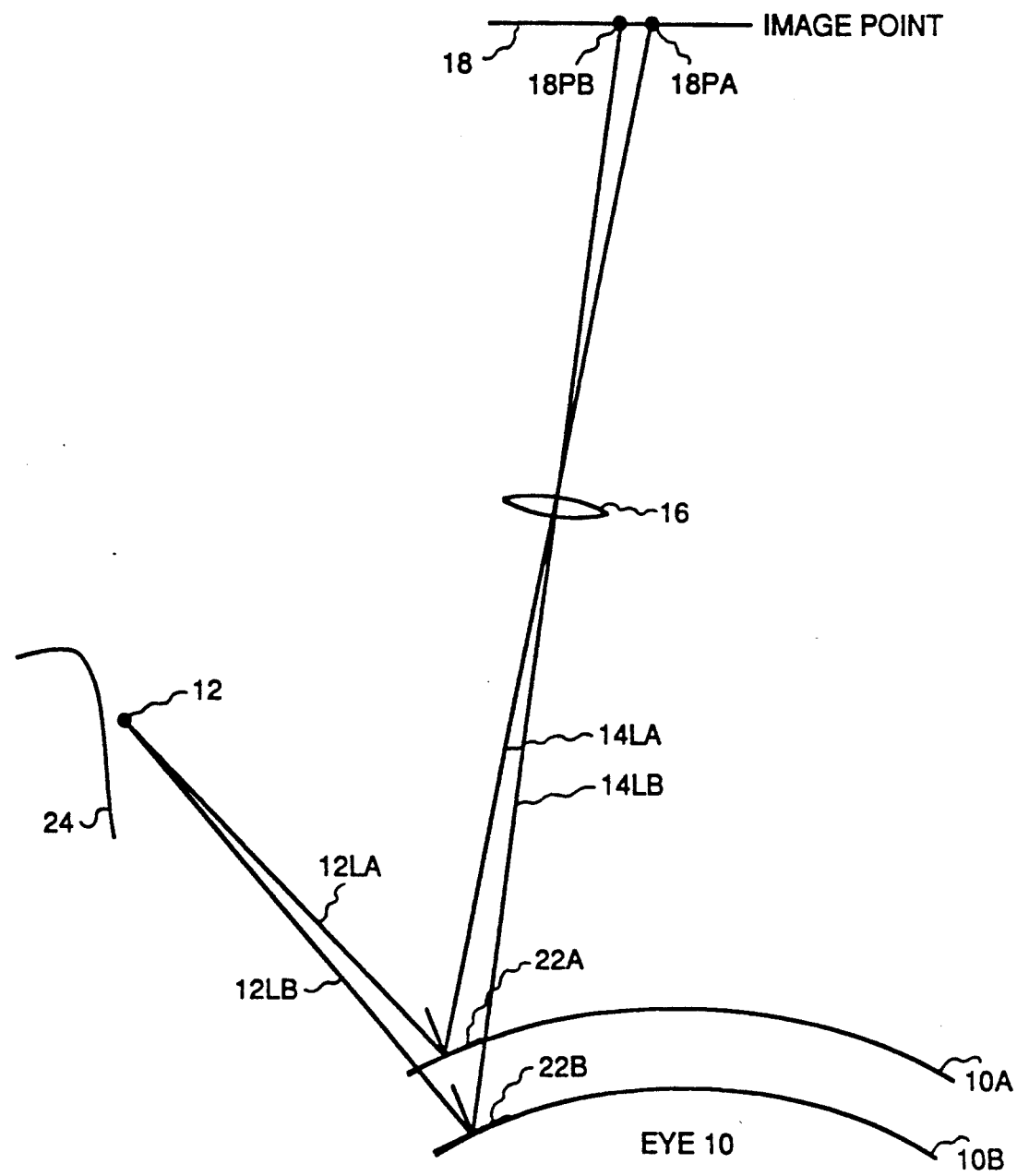
FIG. 1 is a simplified illustration of the source of error in measuring the shape of the cornea with prior art systems.

Before discussing the details of the present invention, reference is made to FIG. 1 for an explanation of the problem with prior art measurement techniques of the cornea. As shown by that simplified conceptual illustration, the measurement of the eye 10 is made by exposing the cornea to a pattern of light. Usually, the pattern of light will be a series of rings, but for ease of illustration, a point source of light 12 (i.e., a point on an unshown ring) is illustrated in FIG. 1. The light from source 12 goes along line 12LB where it strikes the cornea 10B of eye 10 and is reflected (specular reflection) along line 14LB. The reflected beam LB travels through lens 16 to provide an image point 18PB upon an image plane 18. In practice, the image plane 18 would be defined by a TV camera or other image sensing device. The point on cornea 10B where light 12LB is reflected as beam 14LB has a tangent plane 22B. By knowing the position of image point 18PB in the plane 18 and knowing the distance between the image plane and the cornea 10B, one can readily determine the tangent plane 22B which is the curvature of the cornea the at point of light reflection.

If the cornea was assumed to be in position 10A, which is slightly offset form the acutual position 10B, this would introduce an error in the keratometer. This is better understood by considering the case where the cornea is at position 10A. In that case, the light from source 12 would travel along line 12LA and strike a point on cornea position 10A corresponding to tangent plane 22A. With the cornea at position 10A, the light from the reflection at tangent plane 22A would proceed along line 14LA to provide an image point 18PA upon the image plane 18. However, with the cornea at an actual position 10B instead of the assumed position 10A, point source 12 will provide the image point 18PB. In other words, the fact that the cornea is at actual position 10B instead of assumed position 10A will provide a different image point on image plane 18. This difference in the image points causes an error in the measurement.

It can be shown from simple geometric constructions that the error arising from the slight displacement of the actual cornea position 10B from the assumed position 10A will become smaller as the source 12 is moved away from the cornea. However, as shown by FIG. 1, moving the source ring having source point 12 on it may result in the source point 12 being unable to supply light to the cornea 10B because the light will be blocked by the subject's nose 24. In the view of FIG. 1, the source point 12 is about as far as it can be moved from the eye 10 without being blocked by the nose 24. A similar blockage problem may occur with respect to the subject's eyebrows (not shown).

Thus, the subject's nose and eyebrows prevent one from moving some of the rings sufficient far away from the eye 10 in order to minimize the error. If the series of rings is moved beyond the nose and brows, the field of view on the cornea may be severely restricted by interruption of the light by the nose and brows.

Although patterns other than rings may be used, the geometry of FIG. 1 shows that the problem of minimizing error without having the field of view restricted by nose and brows would still occur. Most commercially available keratometers do use illumination by a ring pattern in the form of a disc called a placido (named after the inventor), although other types may be used.

Figure 2:
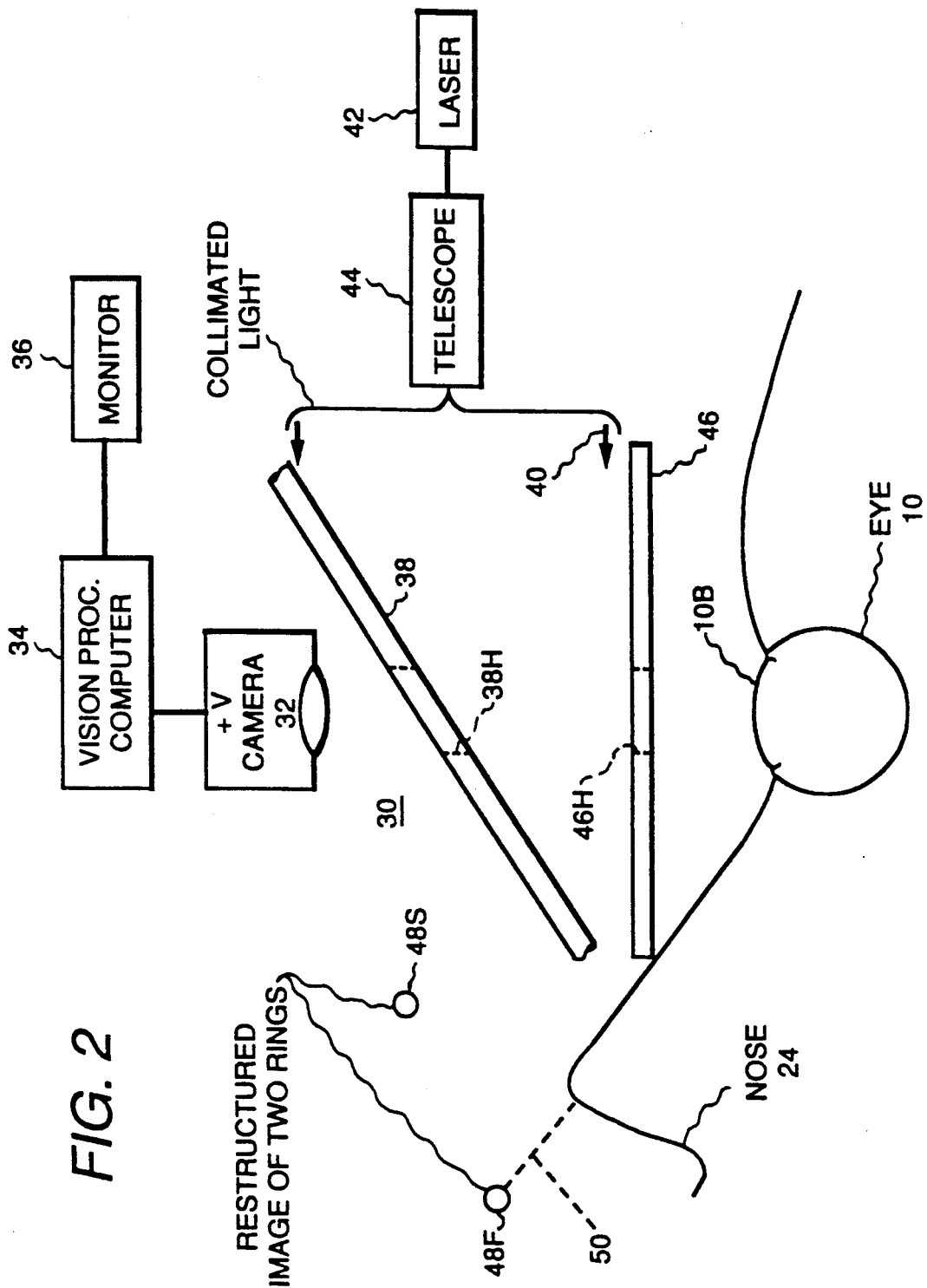
FIG. 2 is a simplified illustration of the present invention as used to measure the eye of a subject.

FIG. 2 shows a preferred embodiment of the system 30 of the present invention together with the eye 10 and nose 24 of a subject. The system 30 includes a TV camera 32, a vision processing computer 34 and a monitor 36, all of which may be constructed using previously known designs. In particular, the TV camera 32 receives an image of a pattern which will be reflected from the cornea 10B of the eye 10. Various known optical elements, not shown, may be used in connection with the TV camera 32. The vision processing computer 34 processes the data from the camera 32 and controls the monitor 36. Additionally, the computer 34 processes the data from the camera 32 to evaluate cornea shape and controls the monitor 36.

Although the system 30 of the present invention may use essentially standard components and processes for processing the image reflected from the cornea, the system 30 uses a quite different technique for placing the image on the cornea 10B. In particular, the system 30 includes a reflecting mirror 38 having a hole 38H disposed therein. The mirror 38 may be circular with the hole 38H located approximately in its center, although other shapes might be used.

Light 40 is applied to the mirror 38. Preferably the light 40 is collimated light from a laser 42 by way of a telescope 44 which is used to increase the beam diameter sufficiently to provide a broad beam which strikes all or most of the reflecting mirror 38. For ease of illustration, the laser 42 and telescope 44 have been shown right next to the mirror 38, it being understood that FIG. 2 is not drawn to scale.

The light 40 is reflected by the mirror 38 so that it strikes a hologram 46 having a hole 46H disposed centrally therein. The hologram 46 would have been previously constructed to provide a plurality of rings imaged at infinity (or other pattern imaged at infinity and useful for measuring the cornea curvature or shape by observation of its reflection in the cornea). An observer looking into the hologram 46 when it is illuminated by light 40 would see a set of rings similar to a placido pattern, but this set would appear to move with the eye position, while otherwise retaining its apparent shape. As shown, the halogram which may be called a hologram means, is between the pattern image and the subject's eye. The hologram or holographic element 46 can be constructed using known methods to produce the ring pattern at infinity. One could create the image of a distant placido using coherent light photography as conventionally accomplished with a number of known holographic techniques.

The hologram 46 provides first and second ring images 48F and 48S. In FIG. 2, only points on these rings are shown for ease of illustration. Additionally, the ring images 48F and 48S are shown relatively close to the eye 10 for simplicity of illustration. In reality, these restructured ring images would be disposed very far away from the eye 10 and effectively at infinity.

The advantage of the use of the hologram 46 will be best understood by noting that the image 48F is disposed in the "shadow" of the nose 24. That is, the line 50 between the image 48F and the cornea 10B is blocked by the nose 24. In other words, it would not be possible to place the ring itself at the location corresponding to 48F. However, the system 30 of the present invention allows one to place that image 48F beyond the nose shadow by using the hologram 46 relatively close to the eye 10. Thus, one can minimize the sensitivity of the system 30 to any error caused by slight displacements of the cornea 10B from its assumed position relative to the camera 32. Additionally, the present invention allows a wide field of view of the cornea 10B without restrictions which would result from interruption of light from distant patterns by the nose and eyebrows.

The holes 38H and 46H respectively disposed in the mirror 38 and the hologram 46 allow the camera 32 to view the reflected pattern image in the cornea 10B. Although one could use transparent material instead of openings to allow light passage from cornea 10B to camera 32, openings avoid spurious reflections which might occur on transparent material. At any rate, windows to allow the reflected pattern image to be viewed by camera 32 are provided (with "windows" meaning a hole for light passage or transparent material for light passage).

The light 40 would preferably be monochromatic collimated light from the laser 42, but the use of any light source sufficient to cause the hologram 46 to project the pattern image would be possible. Preferably, the pattern image would have 10 to 30 rings.

As will be readily appreciated, reflector 38, laser 42, telescope 44, and hologram 46 may be mounted to a common mounting (not shown), and the camera 32 may also be commonly mounted therewith.

The method of the present invention involves the placement of the hologram 46 adjacent to the eye 10 of a subject. More specifically, the hologram 46 is placed between the eye 10 and the nose 24. Light is then applied to the hologram so as to project a pattern image to a location which is relatively distant (i.e., relative to the hologram location) from the eye 10. More specifically, the pattern is a plurality of rings which are imaged at infinity such that an observer looking into the hologram would see the plurality of rings which would appear to move with the eye position, while otherwise retaining the apparent shape of the pattern. The light which is applied to the holographic element or hologram 46 is preferably monochromatic collimated light from a laser, but other light might be used. The light may be applied to the hologram 46 by way of a reflector 38.

Upon the hologram 46 establishing a pattern which is reflected by the cornea 10B, the method involves viewing the reflections of the pattern in the cornea 10B and determining the cornea curvature based upon those reflections.

Although the present application has included specific constructions, it is to be understood that these are for illustrative purposes only. Various modifications and adaptations will be apparent to those of skill in the art. For example, the light might be applied to the hologram 46 by arrangements other than the reflecting mirror 38. In view of this and other possible modifications in the present invention, the scope of the present invention should be determined by reference to the claims which are appended hereto.

What is claimed is:

1. A system for measuring the curvature of a cornea comprising: p1 a hologram means functioning to provide a cornea measurement pattern image such that a reflection of the pattern image on the cornea of the subject's eye is established, wherein the hologram means is between the pattern image and the subject's eye; and a light source for applying light to said hologram means so as to cause it to provide said pattern image.

2. The system of claim 1 wherein said hologram means has a window disposed therein.

3. The system of claim 2 wherein said window in said hologram means is an opening.

4. The system of claim 1 further comprising a reflector and wherein light from said light source is applied to said hologram means by way of reflection from said reflector.

5. The system of claim 4 wherein said reflector has a window disposed therein.

6. The system of claim 5 wherein said window in said reflector is an opening.

7. The system of claim 5 further comprising a viewing subsystem for viewing said reflection of the pattern image on the cornea.

8. The system of claim 7 wherein said viewing subsystem includes a camera, a monitor, and a vision processor for determining cornea curvature based on the reflection of the pattern image on the cornea.

9. The system of claim 7 wherein said hologram means has a window disposed therein and said viewing subsystem views said reflection of the pattern image on the cornea through said window in said reflector and said window in said hologram means.

10. The system of claim 1 wherein said hologram means provides said pattern image imaged at infinity.

11. The system of claim 1 wherein said pattern image includes a plurality of rings.

12. The system of claim 1 wherein said light source applies a fixed beam of light to said hologram means.

13. The system of claim 1 wherein said light source is a laser.

14. The system of claim 13 further comprising means to receive and broaden a beam from said laser before applying a broadened beam to said hologram means.

15. The system of claim 14 wherein said means to receive and broaden is a telescope.

16. A method for measuring the curvature of a cornea comprising the steps of:

placing a hologram in sight of a subject's eye; and applying light to the hologram to provide a cornea measurement pattern image such that a reflection of the pattern image on the cornea of the subject's eye is established, wherein the hologram is between the pattern image and the subject's eye.

17. The method of claim 16 wherein said hologram is placed between the subject's eye and nose.

18. The method of claim 17 wherein said pattern image is imaged at infinity.

19. The method of claim 18 wherein the light is applied from a laser.

20. The method of claim 17 further comprising the step of viewing the reflection of the pattern image on the cornea to determine cornea curvature.

* * * * *